US009474472B2

(12) United States Patent
Baxi

(10) Patent No.: US 9,474,472 B2
(45) Date of Patent: Oct. 25, 2016

(54) APPARATUS, METHOD, AND SYSTEM FOR ACCURATE ESTIMATION OF TOTAL ENERGY EXPENDITURE IN DAILY ACTIVITIES

(71) Applicant: Intel Corporation, Santa Clara, CA (US)

(72) Inventor: Amit S. Baxi, Bangalore (IN)

(73) Assignee: INTEL CORPORATION, Santa Clara, CA (US)

( * ) Notice: Subject to any disclaimer, the term of this patent is extended or adjusted under 35 U.S.C. 154(b) by 239 days.

(21) Appl. No.: 13/726,866

(22) Filed: Dec. 26, 2012

(65) Prior Publication Data

US 2013/0173174 A1     Jul. 4, 2013

(30) Foreign Application Priority Data

Dec. 30, 2011   (IN) ............... 3878/DEL/2011

(51) Int. Cl.
| A61B 5/11 | (2006.01) |
| A61B 5/00 | (2006.01) |
| A61B 5/22 | (2006.01) |
| G06F 19/10 | (2011.01) |
| A63B 24/00 | (2006.01) |
| G06F 19/00 | (2011.01) |

(52) U.S. Cl.
CPC ............ *A61B 5/1123* (2013.01); *A61B 5/222* (2013.01); *A61B 5/6898* (2013.01); *A61B 2503/12* (2013.01); *A61B 2562/0219* (2013.01); *A63B 24/0062* (2013.01); *G06F 19/10* (2013.01); *G06F 19/3481* (2013.01)

(58) Field of Classification Search
None
See application file for complete search history.

(56) References Cited

U.S. PATENT DOCUMENTS

| 5,976,083 | A | * | 11/1999 | Richardson et al. ......... 600/300 |
| 2001/0019598 | A1 | * | 9/2001 | Pyles ................. 377/5 |
| 2007/0060803 | A1 | * | 3/2007 | Liljeryd et al. ............. 600/301 |
| 2008/0190202 | A1 | * | 8/2008 | Kulach ............. A63B 24/0062 73/514.01 |
| 2008/0275348 | A1 | * | 11/2008 | Catt ..................... A61B 5/1112 600/483 |
| 2009/0043531 | A1 | * | 2/2009 | Kahn et al. ................. 702/149 |
| 2009/0171614 | A1 | * | 7/2009 | Damen ................. A61B 5/222 702/141 |
| 2010/0204952 | A1 | * | 8/2010 | Irlam et al. .................... 702/141 |
| 2010/0210975 | A1 | * | 8/2010 | Anthony, III ........ A61B 5/0002 600/595 |
| 2010/0305480 | A1 | * | 12/2010 | Fu ..................... A61B 5/0002 600/595 |
| 2011/0231101 | A1 | * | 9/2011 | Bidargaddi ........... A61B 5/1118 702/19 |
| 2011/0251495 | A1 | * | 10/2011 | Province ................. A61B 5/01 600/483 |
| 2013/0132028 | A1 | * | 5/2013 | Crankson ............. G01C 22/006 702/160 |

(Continued)

OTHER PUBLICATIONS

Ganti, R. K., Srinivasan, S. & Gacic, A. Multisensor Fusion in Smartphones for Lifestyle Monitoring. in International Conference on Body Sensor Networks 36-43 (IEEE, 2010).*

(Continued)

*Primary Examiner* — Soren Harward
(74) *Attorney, Agent, or Firm* — Buckley, Maschoff & Talwalkar LLC

(57) ABSTRACT

An apparatus, article, and system, the apparatus including a housing, a 3-axis accelerometer contained in the housing, a medium storing program instructions, and a processor to execute the program instructions stored in the memory to receive a signal from the 3-axis accelerometer indicative of a user's activities, extract features from the received signals, classify the extracted features into a plurality of activity types, determine a total energy expenditure based on the classification of the extracted features; and provide a report of the total energy expenditure.

12 Claims, 4 Drawing Sheets

(56) References Cited

U.S. PATENT DOCUMENTS

| | | | | |
|---|---|---|---|---|
| 2013/0158686 A1* | 6/2013 | Zhang | ............... | G01C 22/006 700/91 |
| 2013/0281796 A1* | 10/2013 | Pan | ................... | A61B 5/7435 600/301 |

OTHER PUBLICATIONS

Ravi, N., Dandekar, N., Mysore, P. & Littman, M. L. Activity recognition from accelerometer data. in Innovative Applications of Artificial Intelligence 1541-1546 (AAAI Press, 2005).*

Smith, S. W. The Scientist and Engineer's Guide to Digital Signal Processing. (California Technical Publishing, 1999). Excerpt of pp. 277-280.*

Anderson, I. et al. Shakra: Tracking and Sharing Daily Activity Levels with Unaugmented Mobile Phones. Mobile Networks and Applications 12, 185-199 (2007).*

Kwapisz, J. R., Weiss, G. M. & Moore, S. A. Activity Recognition using Cell Phone Accelerometers. ACM SIGKDD Explorations Newsletter 12, 74-82 (2010).*

Pober, D. M., Staudenmayer, J., Raphael, C. & Freedson, P. S. Development of novel techniques to classify physical activity mode using accelerometers. Medicine & Science in Sports & Exercise 38, 1626-34 (2006).*

Puyau, M. R., Adolph, A. L., Vohra, F. A., Zakeri, I. & Butte, N. F. Prediction of activity energy expenditure using accelerometers in in children. Medicine & Science in Sports & Exercise 36, 1625-31 (2004).*

Treuth, M. S. et al. Defining accelerometer thresholds for activity intensities in adolescent girls. Medicine & Science in Sports & Exercise 36, 1259-66 (2004).*

Trost, S. G., Loprinzi, P. D., Moore, R. & Pfeiffer, K. A. Comparison of accelerometer cut points for predicting activity intensity in youth. Medicine & Science in Sports & Exercise 43, 1360-8 (2011).*

Yang, J. Toward physical activity diary: motion recognition using simple acceleration features with mobile phones. In International Workshop on Interactive Multimedia for Consumer Electronics 1 (ACM Press, 2009).*

Zhang, S., Rowlands, A. V., Murray, P. & Hurst, T. L. Physical Activity Classification Using the GENEA Wrist-Worn Accelerometer. Medicine & Science in Sports & Exercise 44, 742-748 (2012).*

* cited by examiner

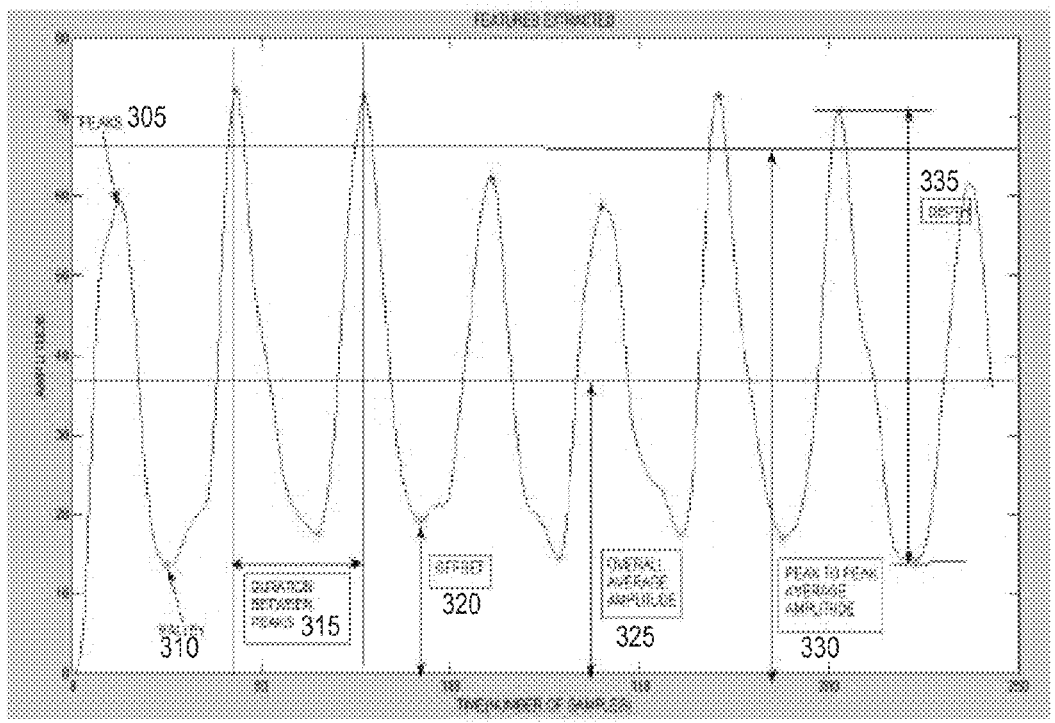
FIG. 3
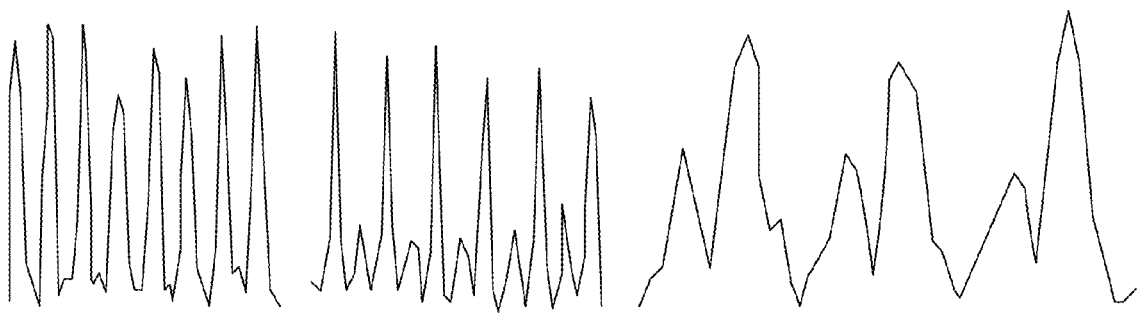
FIG. 4A  FIG. 4B  FIG. 4C

APPARATUS, METHOD, AND SYSTEM FOR ACCURATE ESTIMATION OF TOTAL ENERGY EXPENDITURE IN DAILY ACTIVITIES

The total energy expended by an individual may be tracked for the purpose of wellness, fitness, and overall health monitoring and maintenance. However, determining an accurate measure of such energy expenditures is not easily or efficiently determined using existing devices and methods. For example, motion sensor devices typically only measure high intensity and/or periodic exercise activity. Unfortunately, most individuals only spend a small percentage of their day exercising. Multi-sensor devices purport to measure a wide range of activities. However, these types of devices must typically be worn tight against a user's skin for an extended period of time. Such constraints render these types of devices uncomfortable to wear for their intended purpose and/or duration.

BRIEF DESCRIPTION OF THE DRAWINGS

Aspects of the present disclosure herein are illustrated by way of examples and not by way of limitation in the accompanying figures. For purposes related to simplicity and clarity of illustration rather than limitation, aspects illustrated in the figures are not necessarily drawn to scale. Further, where considered appropriate, reference labels have been repeated among the figures to indicate corresponding or analogous elements.

FIG. 3 is an illustrative depiction of a graph of a signal representative of sensed activities, in accordance with some embodiments herein.

FIGS. 4A-4C illustrate location dependence of a signal, in accordance with an embodiment herein.

DETAILED DESCRIPTION

Figure 1A:
FIGS. 1A-1D are depictions of a device for sensing activities being worn or carried on different locations of a user, in accordance with some embodiments herein.

The disclosure herein provides numerous specific details such regarding a system for implementing various processes and operations. However, it will be appreciated by one skilled in the art(s) related hereto that embodiments of the present disclosure may be practiced without such specific details. Those of ordinary skill in the art will be able to implement appropriate functionality without undue experimentation given the included descriptions herein.

References in the specification to "one embodiment", "some embodiments", "an embodiment", "an example embodiment", "an instance", "some instances" indicate that the embodiment described may include a particular feature, structure, or characteristic, but that every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Some embodiments herein may be implemented in hardware, firmware, software, or any combinations thereof. Embodiments may also be implemented as executable instructions stored on a machine-readable medium that may be read and executed by one or more processors. A machine-readable storage medium may include any tangible non-transitory mechanism for storing information in a form readable by a machine (e.g., a computing device). In some aspects, a machine-readable storage medium may include read only memory (ROM); random access memory (RAM); magnetic disk storage media; optical storage media; flash memory devices; and electrical and optical forms of signals. While firmware, software, routines, and instructions may be described herein as performing certain actions, it should be appreciated that such descriptions are merely for convenience and that such actions are in fact result from computing devices, processors, controllers, and other devices executing the firmware, software, routines, and instructions.

As used herein, the term Total Energy Expenditure refers the total number of calories burned in doing everyday activities (e.g., sitting, walking, cooking, cleaning, etc.). In order to determine the TEE for an individual it is necessary to accurately monitor how active the user is over a period of time performing a range of everyday activities rather than simply measuring only when the person exercises since exercising may typically contribute only 10-20% of the daily calorie burn for the individual.

It is also noted that the term Metabolic Equivalent (MET) is the ratio of the amount of energy consumed in any activity relative to the energy consumed when a person is at rest. It is an index of activity intensity. For example, the energy consumed when a person is sitting quietly is referenced as 1 MET, whereas a slow walk consumes about 2.8 METs and brisk walk about 5 METs. MET values of different activities are available in published literature. A challenge lies in accurately detecting a type of activity and its intensity. In some embodiments, Energy Expenditure in an activity (kcal) =MET value of the activity×weight of person in Kg×time duration in hrs.

Some embodiments herein include an apparatus or device that includes a 3-axis accelerometer. The device including the 3-axis sensor operates to provide signals to a process that determines an estimate of the total daily energy expenditure (TEE) of an individual. In some embodiments, the 3 axes are orthogonal to each other. In some aspects, the 3-axis sensor is sufficient to provide the information that may be needed to determine the TEE. The process to determine the TEE may be embodied as an executable software program or set of instructions.

Figure 1B:
Figure 1C:
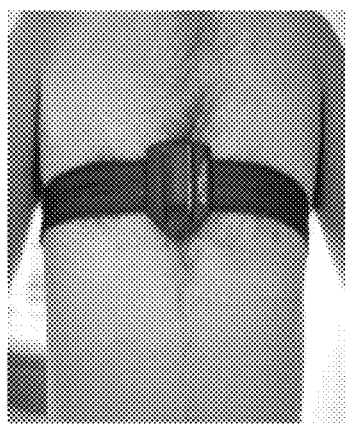
Figure 1D:

FIGS. 1A-1D each illustrate how a device having the 3-axis simulator may be worn on or carried at different locations of a user. It is anticipated that such a device might be worn or attached to one's hip region as shown in FIG. 1A, carried in a shirt pocket as depicted in FIG. 1B, worn next to a user's body during exercising as shown in FIG. 1C. FIG. 1D shows a mobile phone with an integrated 3-axis sensor (not shown in FIG. 1D) running a program or "app" having a user interface that includes an activity monitor. In some instances, the activity monitor may reflect the activities being detected by the device.

While the device may be worn at various locations of a user's body, the user may be asked to indicate where the device is located since the location of the device may impact the parameters being sensed by the device. In some embodiments, the user may be asked to provide or specify input data such as, for example, the location of the device on the user's body, the user's weight, and the user's height.

Figure 2:
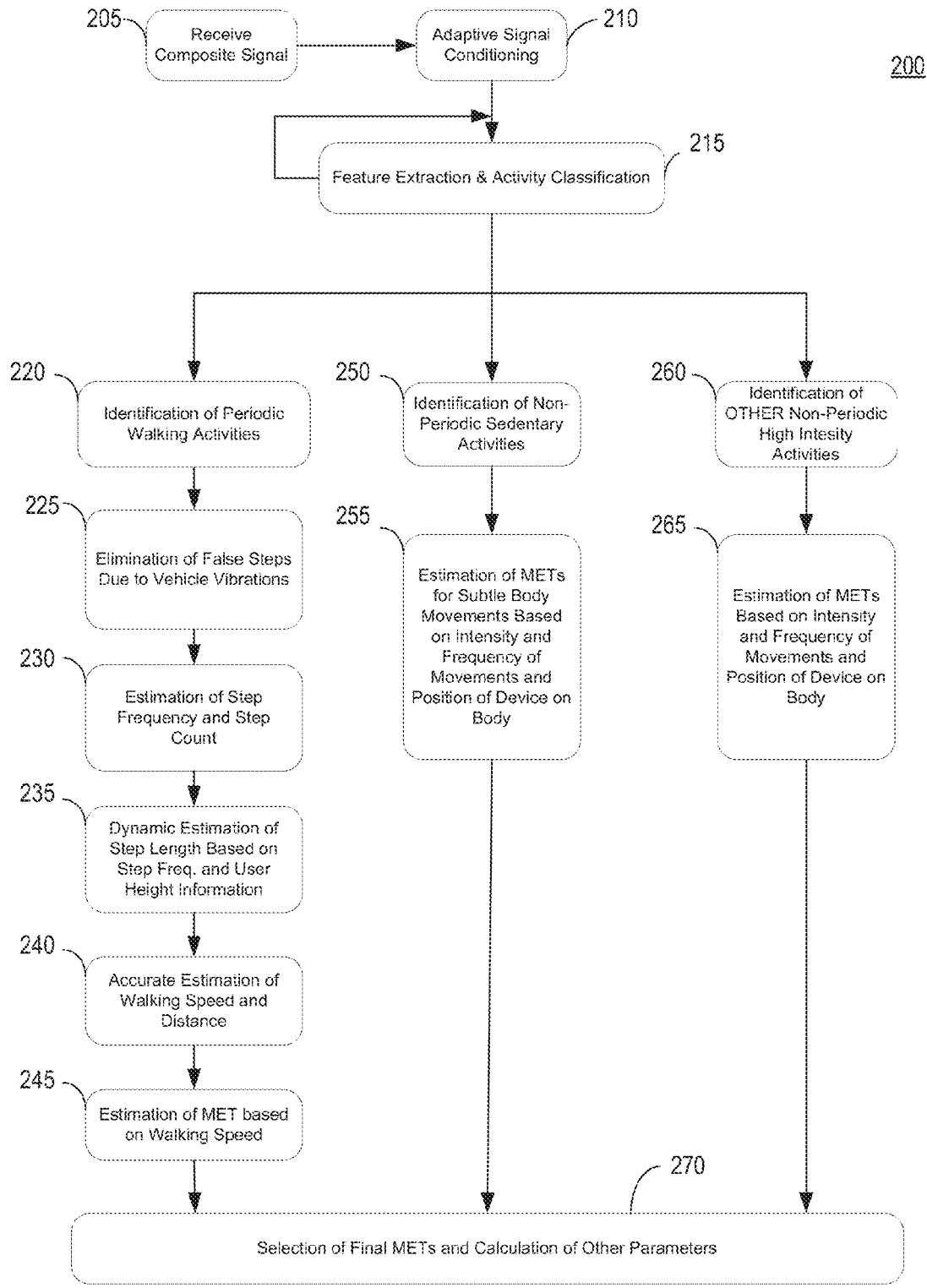
FIG. 2 is a flow diagram of a process, in accordance with some embodiments herein.

FIG. 2 is a flow diagram of a process 200 to provide an accurate estimation of the TEE based on signals received from a 3-axis accelerometer, in accordance with aspects herein. Process 200 generally involves detecting all daily life activities, classifying all daily-life activities into, for example, three categories. The three categories in the present example include (a) walking activities, (b) sedentary activities, (c) "OTHER" moderate intensity activities. Process 200 then applies an optimal EE quantification technique that is tailored to each activity category. Process 200 has been shown to increase the accuracy of determining the TEE.

At operation 205, a composite signal comprising the signals from the 3-axis accelerometer is received. Operation 205 may also calibrate the amount of baseline noise during periods of non-movement for noise compensation.

Operations 210 and 215 may constitute an adaptive feedback control system. The raw composite accelerometer signal received at operation 205 may be adaptively conditioned in real-time by operation 210, based on the features extracted at operation 215.

For the process 200, coefficients of digital filters and moving average windows in operation 210 are dynamically adapted in real-time, based on features (such as mean absolute difference, average magnitude, step frequency and baseline noise) extracted at operation 215. The feedback mechanism including operations 210 and 215 may significantly improve the signal quality for peak detection and other stages. It further dynamic enhancement and preservation of appropriate signal characteristics (amplitude, slope, frequency and temporal components) that change with different walking speeds.

Operation 215 extracts several waveform features from the signal received from operation 210. Some of the features that may be extracted from an incoming signal waveform are depicted in FIG. 3. The extracted features are used as inputs by the subsequent operations of process 200, as well as being used as feedback to control the signal processing parameters (e.g., frequency cut-off of digital filters and moving average windows) of operation 210.

Operation 215 analyzes, in some embodiments, a window or strip (e.g., 5 second sliding window) of the accelerometer's composite signal to detect the various features such as peaks and valleys by examining the turning points and creates a record or table of the peaks and valleys and temporal locations of the peaks and valleys. Once the table or record is established, secondary features such as, for example, the duration between peaks, their periodicity, signal offset, signal depth, etc. may be extracted or derived.

As shown in FIG. 3, some of the features that may be extracted from a waveform 300 include a peak value 305, a low or valley value 310, a duration between peaks 315, an offset 320, an overall average amplitude 325, a peak-to-peak average amplitude 330, and a depth value 335 for the waveform. These are some of the values that may be determined and extracted from a received signal waveform at operation 215. In some embodiments, other or different features may be extracted although not shown in FIG. 3.

Based on the extracted features, the sensed activities may be classified into a plurality of categories. In the example of FIG. 2, the recorded activity is classified into one of 3 types of activities. Each type of activity is processed independently to produce an optimal EE estimation that is specifically tailored to the particular activity type. The activity may be classified as "walking" activities that are characterized by periodic signals and may cover a range of slow walking to running (operations 220-245); "sedentary" activities characterized by non-periodic low intensity activities that have a MET<3 (operations 250-255); and "Other" activities characterized as being non-periodic and high intensity that have a MET>3 (operations 260-265).

The "walking" activities processed by operations 220-245 are characterized by periodic signals and may cover a range of slow walking to running activities. However, the signal received may vary depending on the location the device is worn or carried by a user. FIGS. 4A-4C are examples of the same activity but with the device located on a user's chest (4A) and the user's hip (4B), with FIG. 4C showing the temporal variations between consecutive steps. In the instance the device is located on the user's hip, there are significantly higher amplitude variations as shown in FIGS. 4A and 4B and temporal variations as shown in FIG. 4C between consecutive steps when the device is worn on the hip as compared to the chest location.

For activities identified as "walking" activities", process 200 proceeds to operation 220. At operation 225, processing is performed to eliminate false steps. In some instances, false steps may be due to vibrations caused by moving vehicles. By filtering out the high frequencies consist with vehicle travel, these types of false steps may be eliminated. Operation 230 estimates the step frequency and step count of the user and operation 235 is a real-time, dynamic estimation of the user's step length based on step frequency and the user's height. The user may be asked to provide their height so that the processes herein may make an accurate estimation of their step length. It is noted that process 200 does not assume a fixed or static step length since the step length of a person may vary. Operation 240 calculates an accurate estimation of the "walking" speed and distance. Based on the estimated "walking" speed and distance, the user's METs can be determined at operation 245. The calculated METs are provided to operation 270 for a final MET (e.g., aggregate) and other parameters determination and reporting.

Activities are classified as "sedentary" at operation 250 due to the activity signals indicating non-periodic and low intensity movements such as desk work, low intensity housework, or general "at-rest" activities. Operation 255 generates an estimation of METs for this type of subtle movements based on an intensity and frequency of movements and the position of the 3-axis accelerometer device on the body of the user. The calculated METs are provided to operation 270 for a final MET and other parameters determination and reporting.

Activities are classified as "other" activities at operation 260 due to the activity signals indicating non-periodic and high intensity movements such as playing, gardening, mopping, etc. Operation 265 generates an estimation of METs for this type of behaviors based on an intensity and frequency of movements and the position of the 3-axis accelerometer device on the body of the user. The calculated METs are provided to operation 270 for a final MET and other parameters determination and reporting.

Operation 270 may generate reports and records that include, for example, a step count, walking speed, distance "walked", activity type, and energy expenditure (e.g., total EE, Active EE, Activity METs, Physical Activity Level, etc.). The final MET calculation may be an aggregate of the individual METs and may be generated by the device worn by the user or the data need to generate the reports may be transmitted to another device for further processing. The transmission from the device may be wired (e.g., via a USB cable) or wireless (e.g., WiFi or Bluetooth).

Figure 5:
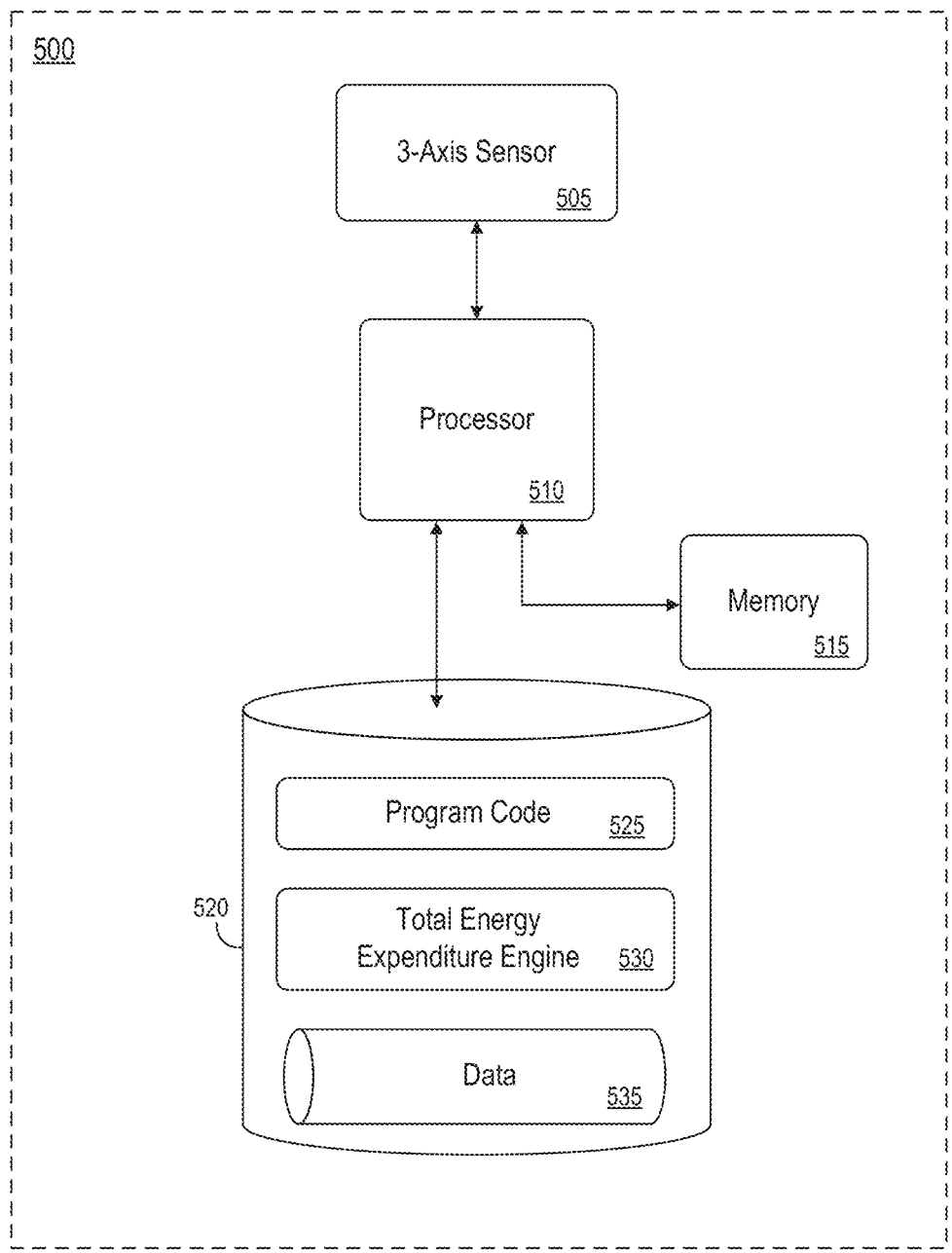
FIG. 5 is an illustrative block diagram of an apparatus, in accordance with some embodiments herein.

FIG. 5 is a block diagram of a system or apparatus 500 according to some embodiments. System 500 may be, for example, associated with any device to implement the methods and processes described herein, including for example a device including a 3-axis accelerometer that may be worn on the body of a user. System 500 comprises a processor 505, such as one or more commercially available Central Processing Units (CPUs) in the form of one-chip microprocessors or a multi-core processor, coupled to a 3-axis sensor (e.g., an accelerometer). System 500 may also include a local memory 515, such as RAM memory modules. The system 500 may further include, though not shown, an input device (e.g., a touch screen and/or keyboard to enter user input content) and an output device (e.g., a display screen, a light, a speaker, etc.).

Processor 510 communicates with a storage device 520. Storage device 520 may comprise any appropriate information storage device. Storage device 520 stores a program code 525 that may provide processor executable instructions for processing requests in accordance with processes herein. Processor 510 may perform the instructions of the program 525 to thereby operate in accordance with any of the embodiments described herein. Program code 525 may be stored in a compressed, uncompiled and/or encrypted format. Program code 525 may furthermore include other program elements, such as an operating system and/or device drivers used by the processor 510 to interface with, for example, peripheral devices. Storage device 520 may also include data 535. Data 535, in conjunction with Total Energy Expenditure Engine 530, may be used by system 500, in some aspects, in performing the processes herein, such as process 200.

All systems and processes discussed herein may be embodied in program code stored on one or more tangible computer-readable media.

Embodiments have been described herein solely for the purpose of illustration. Persons skilled in the art will recognize from this description that embodiments are not limited to those described, but may be practiced with modifications and alterations limited only by the spirit and scope of the appended claims.

What is claimed is:

1. An apparatus comprising:
a housing;
a 3-axis accelerometer contained in the housing;
a medium storing program instructions; and
a processor to execute the program instructions stored in the memory to:
receive a signal from the 3-axis accelerometer indicative of a user's activities;
receive an indication of a location of the housing on the user's body;
extract features from the received signals based on the location of the housing on the user's body and by examining turning points of the received signal, the extracted features comprising peaks and valleys associated with the turning points of the received signal from the 3-axis accelerometer;
classify the extracted features into activity types consisting of (i) activities characterized by periodic signals having a range of slow walking to running, (ii) activities characterized by non-periodic low intensity activities that have a metabolic equivalent less than 3, (ii) activities characterized as being non-periodic and high intensity that have a metabolic equivalent greater than 3;
determine a total energy expenditure based on the classification of the extracted features by processing each type of activity independently to produce an optimal energy expenditure estimation tailored to the particular activity type; and
provide a report of the total energy expenditure.

2. The apparatus of claim 1, wherein the determination of the total energy expenditure is further based on a location of the device on the user.

3. The apparatus of claim 1, further comprising the processor to:
determine, for the periodic activity type, an estimation of a step frequency and a step count; and
generate a dynamic estimate of a step length based on the step frequency and user height information.

4. The apparatus of claim 1, further comprising the processor to determine an estimation of metabolic equivalents based on an intensity of the activities and a position of the apparatus on the body of the user.

5. The apparatus of claim 1 wherein the peaks and valleys associated with the received signal from the 3-axis accelerometer are stored with temporal locations of the peaks and valleys.

6. The apparatus of claim 5, wherein a duration between peaks and their periodicity are derived from the stored peaks and valleys and their associated temporal locations.

7. The apparatus of claim 1, wherein the extracted features are used to control a frequency cut-off of digital filters.

8. The apparatus of claim 1, wherein the extracted features are used to control a moving average window.

9. A system comprising:
a memory;
a housing;
a 3-axis accelerometer contained in the housing;
a medium storing program instructions; and
a processor to execute the program instructions stored in the memory to:
receive a signal from the 3-axis accelerometer indicative of a user's activities;
receive an indication of a location of the housing on the user's body;
extract features from the received signals based on the location of the housing on the user's body and by examining turning points of the received signal, the extracted features comprising peaks and valleys associated with the turning points of the received signal from the 3-axis accelerometer;
classify the extracted features into activity types consisting of (i) activities characterized by periodic signals having a range of slow walking to running, (ii) activities characterized by non-periodic low intensity activities that have a metabolic equivalent less than 3, (ii) activities characterized as being non-periodic and high intensity that have a metabolic equivalent greater than 3;
determine a total energy expenditure based on the classification of the extracted features by processing each type of activity independently to produce an optimal energy expenditure estimation tailored to the particular activity type; and
provide a report of the total energy expenditure.

10. The system of claim 9, wherein the determination of the total energy expenditure is further based on a location of the device on the user.

11. The system of claim 9, further comprising:
determining, for the periodic activity type, an estimation of a step frequency and a step count; and generating a dynamic estimate of a step length based on the step frequency and user height information.

12. The system of claim 9, further comprising determining an estimation of metabolic equivalents based on an intensity of the activities and a position of the housing on the body of the user.

* * * * *